United States Patent [19]

Sinnreich

[11] 4,083,369
[45] Apr. 11, 1978

[54] SURGICAL INSTRUMENTS

[76] Inventor: Manfred Sinnreich, 160 Ft. Hill Rd., Scarsdale, N.Y. 10583

[21] Appl. No.: 702,191

[22] Filed: Jul. 2, 1976

[51] Int. Cl.² ............ A61M 1/00; A61M 25/00; A61M 29/02
[52] U.S. Cl. .................. 128/276; 128/344; 128/349 B; 128/350 R; 128/DIG. 9
[58] Field of Search ........... 128/242, 246, 344, 349 B, 128/DIG. 9, 350 R, 349 BV, 276

[56] References Cited

U.S. PATENT DOCUMENTS

| | | | |
|---|---|---|---|
| 612,724 | 10/1898 | Hamilton | 128/344 |
| 1,719,428 | 7/1929 | Friedman | 128/242 |
| 2,638,093 | 5/1953 | Kulick | 128/344 X |
| 3,049,125 | 8/1962 | Kriwkowitsch | 128/344 X |
| 3,626,949 | 12/1971 | Shute | 128/344 |
| 3,877,838 | 4/1975 | Choy | 128/344 X |
| 3,905,361 | 9/1975 | Hewson et al. | 128/276 X |
| 4,040,413 | 8/1977 | Ohshiro | 128/6 |

*Primary Examiner*—Robert W. Michell
*Assistant Examiner*—Michael H. Thaler
*Attorney, Agent, or Firm*—Charles E. Temko

[57] ABSTRACT

The invention relates to surgical instruments having particular application to the field of gynecology. The disclosure includes an inflatable packing and continuous suction device suitable for use following hysterectomy procedures to assist in normal draining while maintaining the bowel in properly elevated condition. There is also disclosed an improved trocar shield useful in performing various procedures. Both embodiments are characterized in the provision of a relatively rigid hollow tube element having mounted thereon an expandable balloon element in which portions thereof are of differential thickness whereby the configuration attained at equilibrium may be predetermined.

3 Claims, 3 Drawing Figures

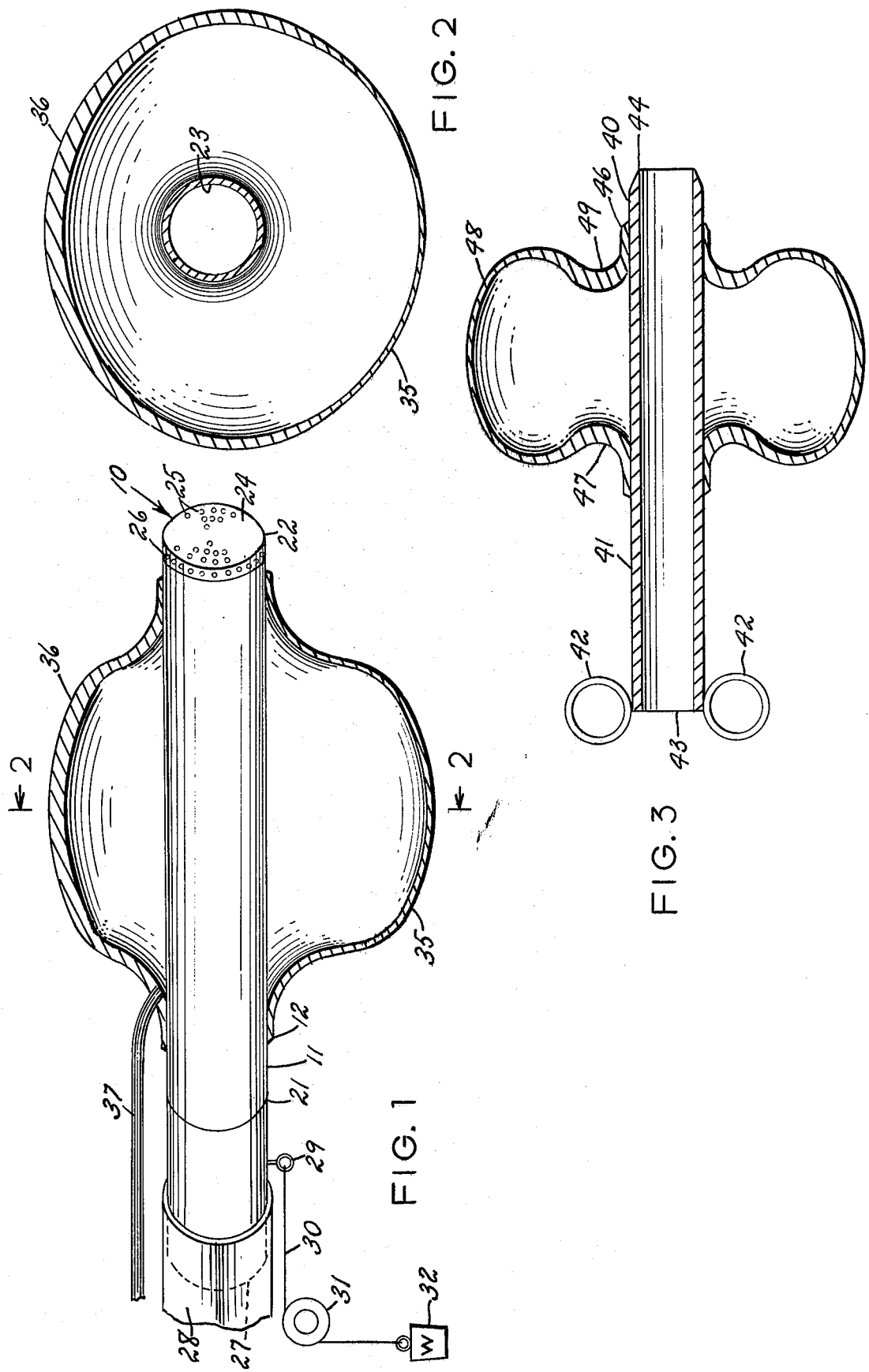

SURGICAL INSTRUMENTS

BACKGROUND OF THE INVENTION

In my prior U.S. Pat. No. 3,882,852 granted Apr. 13, 1975, there is disclosed a device for dilating the uterus comprising a hollow rigid tube upon which an inflatable balloon is mounted in coaxial relation. The tube serves as a conduit-forming member for the introduction of an endoscope or other surgical instrument, and the balloon serves to dilate the uterine cavity so that the surgical procedure may be performed by structure disposed at the distal end of the tube element. So-called Foley catheters are also known in the art, and are used for dilation purposes. But owing to the absence of a rigid element, they do not have useful application in the field of gynecological surgery.

SUMMARY OF THE INVENTION

Briefly stated, the invention contemplates the provision of an improved device resembling to some degree that described in the above mentioned patent, including an axially disposed rigid tube element, and a surrounding balloon-like inflatable element in which the configuration of the balloon has been modified to enable the same be used as a pneumatic packing and drainage device following a hysterectomy procedure. The axially disposed tube element serves to interconnect the cavity with a source of gentle suction applied to the proximal end of the tube element whereby drained matter is continuously removed. One half of the inflatable element expands at a greater rate than the other, and is positioned to face the spine and pelvis of the patient, whereby the tube may be axially aligned with the vagina when positioned in the surgical cavity. The thinner section of the inflatable element may be suitably coated with an antiseptic emollient which directly contacts the raw tissue exposed with partial removal of the peritoneum. Another embodiment in the form of an improved trocar shield is provided with an inflatable element which, on inflation, assumes the contour of a torus thereby distending the cavity in which it is placed, and allowing adequate space on the distal side of the tubular member to perform surgical procedures. This is accomplished by making the inflatable element in such manner that it includes three coaxially aligned portions, the outer two of which are relatively thicker in cross section that the centrally disposed portion.

BRIEF DESCRIPTION OF THE DRAWING

In the drawing, to which reference will be made in the specification, similar reference characters have been employed to designate corresponding parts throughout the several views.

FIG. 1 is a schematic view in perspective, partially in section of a first embodiment of the invention.

FIG. 2 is a sectional view as seen from the plane 2—2 in FIG. 1.

FIG. 3 is a schematic perspective view, partially in section of a second embodiment of the invention.

DETAILED DESCRIPTION OF THE DISCLOSED EMBODIMENTS

In accordance with the first embodiment of the invention, the device, generally indicated by reference character 10, comprises broadly: a hollow tubular element 11 and an inflatable element 12.

The tubular element 11 may be formed of metallic or synthetic resinous materials, either as a molded, cast or extruded product. It is bounded by an outer cylindrical surface 20 extending between a proximal end 21 and a distal end 22. A continuous bore 23 extends between said ends, and terminates at the distal end thereof in a perforated end wall 24 having a plurality of apertures 25 of approximately 1mm. diameter. Extending through the wall of the tubular element adjacent the distal end are a plurality of openings 26, also preferably of 1mm. diameter.

Secured to the proximal end 21 is an adapter 27 serving to connect the device with a source of low pressure suction 28. The adapter 27 mounts a loop member 29 engaging a tensed cord 30 entrained over a pulley 31 supported by a portion of the bed of the patient (not shown) there being a weight 32 secured to the opposite end.

The inflatable element 12 is preferably formed from natural or synthetic surgical grade elastomers, and is cylindrical in configuration as well as asymmetric along its principal longitudinal axis. It thus includes a relatively thin wall area 35 and a relatively thicker wall area 36. Air tube 37 is preferably molded integrally with the thicker area 36, and as the same will normally project outwardly of the cavity after positioning, it serves as an indexing means as well.

When the device 10 is positioned within a surgical cavity previously occupied by the uterus, it is positioned in such manner that the thinner sections face the spine and pelvis of the patient, and the thicker section the forward abdominal wall. With inflation, the tube element will be positioned in line with the vagina with its axis in eccentric relation with respect to the expandable element. A source of suction is applied to the adapter 27, which will result in the drainage of matter from the cavity on a continuous basis. The expanding element in the thinner areas contacts the raw tissues exposed by partial removal of the peritoneum, and may be coated with a suitable emollient in the form of an antibiotic ointment known in the art (not shown). Aside from promoting healing, the ointment effectively prevents sticking of the inflatable element when the time for removal has arrived. With healing, the degree of inflation may be lessened prior to ultimate removal.

The second embodiment, generally indicated by reference character 40 is suitable for use with a wide variety of surgical procedures, and is illustrated in the form of a trocar shield. Like the first embodiment, it includes an inflatable element having portions of differential thickness to control the shape of the expandable element at equilibrium.

Referring to FIG. 3, the second embodiment includes a tubular element 41 having a manually engagable means 42 at a proximal end 43, and a tapered feather edge 44 at a distal end 45 thereof. This edge may be formed as a synthetic resinous insert, or, where the tube itself is formed from synthetic resinous materials, it may be formed as a result of a molding operation. By providing a feather edge, there is no tendency for portions of pierced tissue to engage the edge, and the puncture obtained is performed smoothly. Once inside the body, the trocar itself (not shown) may be removed, and the inflatable element 46 expanded. The element 46 includes first, second and third bands 47, 48 and 49, respectively, of annular configuration, the planes of which are disposed substantially perpendicular to that of the shield element 41. The first and third bands 47 and 49, respectively, are formed of material which is substantially thicker than that of the second band 48 disposed therebetween. Thus, with inflation, the expanded element, because of the differential thickness of the bands 47–49 assumes a quasi-toroidal shape at equilibrium.

It will be understood that the inflatable element has application with surgical instrumentation other than a trocar shield. For example, it can be placed upon or used on conjunction with an endoscope, as disclosed in my above mentioned prior patent. The quasi-toroidal shape causes the surgical cavity to be expanded for completion of a surgical procedure, and pushes the cavity in such manner that adquate space not occupied by the expandable element is available at the distal end of the tube, this configuration adding significant space availability as contrasted with the expandable element of uniform thickness disclosed in my above mentioned patent.

I wish it to be understood that I do not consider the invention limited to the precise details of structure shown and set forth in this specification, for obvious modifications will occur to those skilled in the art to which the invention pertains.

I claim:

1. An improved surgical device comprising: a hollow circular cylindrical tube element having an outer surface extending between proximal and distal ends, and having an expandable element of generally circular cylindrical configuration having first and second end edges secured to said outer surface; said expandable element having surface areas of differential thickness which are oppositely disposed relative to the longitudinal axis of said tube element; whereby upon expansion, the axis of the tube element is displaced to a non-central relation relative to said inflatable element.

2. A surgical device in accordance with claim 1, further characterized in said tube element having a perforated end wall at said distal end thereof, means interconnecting said proximal end with a source of pneumatic suction; and means including a tensed cord and a weight tensing said cord connected to said tubular element, to maintain said device in position against the action of suction applied to said tubular element, whereby said device may be inserted in a body cavity and maintained in position therein after installation.

3. An improved surgical device comprising: a hollow circular cylindrical tube element having an outer surface extending between proximal and distal ends, said distal end being tapered to a feather edge; said tube element having an expandable element of generally circular cylindrical configuration, having first and second edges secured to said outer surface; said expandable element having surface areas of differential thickness, whereby upon expansion under pressure of an injected fluid, said expandable element will assume a predetermined configuration conforming to a surgical cavity in which said device is positioned; said inflatable element having three parallel circumferentially disposed surface areas, the axes of which are parallel to the longitudinal axis of the tube element, two of said areas having relatively thick cross section, and a third area, disposed between said first and second areas having a relatively thin cross section, whereby upon expansion, said expandable element assumes a quasi-toroidal configuration.

* * * * *